(12) United States Patent
Walter

(10) Patent No.: US 9,304,064 B2
(45) Date of Patent: Apr. 5, 2016

(54) KNIFE HOLDER HAVING A BLADE CHANGING APPARATUS

(71) Applicant: Leica Biosystems Nussloch GmbH, Nussloch (DE)

(72) Inventor: Roland Walter, Reilingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 486 days.

(21) Appl. No.: 13/948,250

(22) Filed: Jul. 23, 2013

(65) Prior Publication Data
US 2014/0033888 A1 Feb. 6, 2014

(30) Foreign Application Priority Data

Aug. 3, 2012 (DE) .......................... 10 2012 213 824

(51) Int. Cl.
*G01N 1/06* (2006.01)
*B23Q 3/155* (2006.01)

(52) U.S. Cl.
CPC *G01N 1/06* (2013.01); *B23Q 3/155* (2013.01); *G01N 2001/061* (2013.01); *Y10S 83/9155* (2013.01); *Y10S 83/954* (2013.01); *Y10T 83/6492* (2015.04); *Y10T 83/6499* (2015.04); *Y10T 83/9457* (2015.04); *Y10T 483/17* (2015.01)

(58) Field of Classification Search
CPC ............ Y10T 483/17; Y10T 483/1729; Y10T 483/1731; Y10T 83/6492; Y10T 83/6499; Y10S 83/9155; Y10S 83/954; G01N 1/06

USPC ........ 483/16, 28–29; 83/915.5, 954, 703, 707
See application file for complete search history.

(56) References Cited

U.S. PATENT DOCUMENTS

| | | | | |
|---|---|---|---|---|
| 2,653,379 | A | * 9/1953 | Austin | .................... B26B 21/24 30/40.2 |
| 4,207,790 | A | 6/1980 | Endo | |
| 4,700,600 | A | 10/1987 | Pickett | |
| 8,187,157 | B2 | * 5/2012 | Thiem | ...................... B26D 7/00 483/16 |
| 9,033,184 | B2 | * 5/2015 | Walter | .................. B65D 83/08 221/102 |
| 2002/0005104 | A1 | 1/2002 | Hendrick et al. | |
| 2006/0272467 | A1 | 12/2006 | Hendrick et al. | |
| 2008/0148918 | A1 | 6/2008 | Thiem et al. | |
| 2008/0202308 | A1 | 8/2008 | Fujiwara et al. | |
| 2009/0235799 | A1 | 9/2009 | Thiem | |

FOREIGN PATENT DOCUMENTS

WO 01/84110 A2 11/2001

\* cited by examiner

*Primary Examiner* — Erica E Cadugan
(74) *Attorney, Agent, or Firm* — Hodgson Russ LLP

(57) ABSTRACT

The invention relates to a knife holder (100) having a blade changing apparatus (102). The knife holder has a first blade receptacle (111) defining a cutting position, a securing device (130, 141, 142) for securing a blade (201) received in the first blade receptacle (111), a second blade receptacle (112) defining an output position, and an ejection device (141, 143, 144*a*) for ejecting a blade (201) received in the first blade receptacle (111) out of the first blade receptacle (111). The first and the second blade receptacles are arranged in the knife holder in such a way that a blade ejected from the first blade receptacle (111) can travel by gravity into the second blade receptacle (112).

11 Claims, 5 Drawing Sheets

KNIFE HOLDER HAVING A BLADE CHANGING APPARATUS

CROSS REFERENCE TO RELATED APPLICATIONS

This application claims priority of German patent application number 10 2012 213 824.2 filed Aug. 3, 2012, the entire disclosure of which is incorporated by reference herein.

FIELD OF THE INVENTION

The present invention relates to a knife holder having a blade changing apparatus for a microtome.

BACKGROUND OF THE INVENTION

Microtomes are used, for example, to prepare thin sections of tissue that can then be investigated microscopically. Microtomes have for this purpose a knife holder having a very sharp blade. Disposable blades have become established in particular in the laboratory sector, a blade being disposed of after a number of sectioning operations and replaced with a new blade. One such knife holder is described in DE 10 2004 051 974 A1. Here the blades must be changed manually. As an improvement, DE 10 2007 006 826 B1 describes a knife holder in which blade changing is assisted by a driver. New blades are taken out of a blade supply container in which a blade stack made up of multiple blades is received in spring-loaded fashion, and are slid into a blade receptacle. A used blade present in the blade receptacle is thereby pushed backward out of the blade receptacle and disposed of into a blade disposal container. This design requires a relatively large amount of space. The sliding out of the used blade can also be impeded, for example, by jamming or oversliding.

It is desirable to have available a blade changing apparatus that is improved in particular in this regard.

SUMMARY AND ADVANTAGES OF THE INVENTION

The present invention proposes a knife holder for a microtome, wherein the knife holder has a blade changing apparatus.

In a knife holder according to the present invention, a used blade no longer needs to be pushed out of the blade receptacle of the cutting position (hereinafter the "first blade receptacle") by a new blade. Instead, it can be delivered by means of gravity, e.g. can fall or slide or slip out, into a blade receptacle of a disposal position (hereinafter the "second blade receptacle"). A new blade can then be slid into the unoccupied blade receptacle of the cutting position so that no risk of jamming or oversliding exists. The particular configuration also makes it possible for the used blade to be disposed of to the side on which the new blades are also located, so that the width of the knife holder can be reduced. Instead of three blade lengths as in the existing art, only two blade lengths are now needed.

A securing means, e.g. a clamping mechanism, for securing a blade in the first blade receptacle, and an ejection means, e.g. a movable lug, for ejecting a blade received in the first blade receptacle out of the first blade receptacle, are usefully connected to the same actuation means, e.g. to a lever, in order to be actuated thereby.

In a preferred embodiment, the first blade receptacle and the second blade receptacle are arranged vertically spaced apart in the knife holder. This is a particularly simple construction for utilizing gravity, without which, for example, a relative motion of the receptacles with respect to one another would be necessary, for example by rotating or tilting the knife holder.

The knife holder is preferably equipped with an external mounting location for a blade supply container that contains unused or new blades, and with a first, in particular automatic or manually actuated driver in order to convey a new blade out of the externally mounted blade supply container into the first blade receptacle. The external mounting location results in a defined position and orientation for the blade supply container, so that the insertion of a new blade into the blade receptacle can occur in particularly simple fashion via the first driver. This considerably reduces a risk of injury, since the user no longer needs to touch the blade.

The knife holder is preferably also equipped with an external mounting location for a blade disposal container, separated from the blade supply container, into which used or old blades are discarded, and with a second, in particular automatic or manually actuated driver in order to convey a used blade out of the second blade receptacle into the externally mounted blade disposal container. The external mounting location results in a defined position and orientation for the blade disposal container, so that the discarding of a new blade into the blade disposal container can occur in particularly simple fashion via the second driver. This considerably reduces a risk of injury, since the user no longer needs to touch the blade.

In order to minimize the installation space, an external mounting location is usefully located horizontally directly next to the associated blade receptacle.

Further advantages and embodiments of the invention are evident from the description and from the appended drawings.

It is understood that the features recited above and those yet to be explained below are usable not only in the respective combination indicated, but also in other combinations or in isolation, without departing from the scope of the present invention.

The invention is schematically depicted in the drawings on the basis of an exemplifying embodiment, and will be described in detail below with reference to the drawings.

BRIEF DESCRIPTION OF THE DRAWING VIEWS

FIGS. 1a through 1d show various steps of a blade changing operation, with reference to a knife block of a knife holder according to a preferred embodiment of the invention, FIG. 2 is a perspective view of elements of the blade changing apparatus in addition to the knife block, FIG. 3 is a perspective view of the substantially complete knife holder with the blade changing apparatus, FIG. 4 is a cross-sectional view of the knife holder in the region of the blade changing apparatus, and FIG. 5 is a cross-sectional view of the knife holder in the region of the knife block.

DETAILED DESCRIPTION OF THE INVENTION

The Figures are described below together and continuously, identical elements being labeled with identical reference characters.

FIGS. 1a to 1d show various steps or states of a blade changing operation with reference to a schematic depiction of a few elements of a knife holder 100. The sequence of FIGS. 1a to 1d corresponds to the sequence in time. FIG. 2 shows knife holder 100, with elements of a blade changing apparatus 101, in a state according to FIG. 1c.

FIG. 3 is a schematic, perspective view of knife holder 100 with further elements for better clarity, and FIGS. 4 and 5 each show a cross-sectional view through knife holder 100.

A knife block 110 of a knife holder 100 is depicted, comprising in its upper region two steps 111 and 112 that each form a blade receptacle. Step 111 forms a first blade receptacle for a cutting position, and step 112 forms a second blade receptacle for a disposal position. A blade that is located in first blade receptacle 111 is labeled 200.

Depicted at the same height, next to blade receptacle 111, is a blade stack 210 that is usually received in a blade supply container (not depicted in FIG. 1). As indicated by arrow 1, a new blade has been delivered into first blade receptacle 111 by being slid out of the blade supply container. In this state only one blade is present in first blade receptacle 111.

For disposal of the blade, it is firstly ejected out of first blade receptacle 111 as indicated by an arrow 2 in FIG. 1b so that it can fall by gravity into second blade receptacle 112. In this state only one blade is present in second blade receptacle 112.

The next step of the blade changing operation is depicted in FIG. 1c. A (new) blade 201 to be utilized is located in the blade stack, and the (old) blade to be disposed of is located in blade receptacle 112 for the disposal position. As indicated by an arrow 3, blade 201 is then delivered into blade receptacle 111 and, as indicated by arrow 4, blade 200 is delivered into a disposal container that, according to a preferred embodiment of the invention, is arranged on the same side as the blade supply container. The two conveying operations can be carried out simultaneously but also successively. One or both conveying operations can each be carried by a driver that engages into engagement openings that are depicted in the Figure as holes in the blade.

The final state is depicted in FIG. 1d: new blade 201 is located in first blade receptacle 111 and can be secured there, and old blade 200 has been conveyed out of second blade receptacle 112 and can fall, for example, into a blade disposal container.

FIG. 2 shows the state according to FIG. 1c; schematically depicted to the left next to knife block 110 is a driver mechanism 300 of blade changing apparatus 101, which mechanism comprises a first driver 301 for new blade 201 as well as a second driver 302 for old blade 200.

The first and the second driver are coupled to a driving mechanism, embodied as a toothed linkage 303, on which a driver actuation element 304 acts. Proceeding from the position shown in FIG. 2, upon actuation of driver actuation element 304, by means of the drivers new blade 201 is conveyed to the right into first receptacle 111, and old blade 200 is conveyed to the left out of second receptacle 112.

First driver 301 possesses a driver spring plate 305 that can be moved back and forth by a driver toothed rack 306 and is mounted on a driver guide 307. Second driver 302 is embodied substantially as a driver toothed rack having a blade stop 302a, e.g. a pin, at its right end in FIG. 2.

Figure 5:
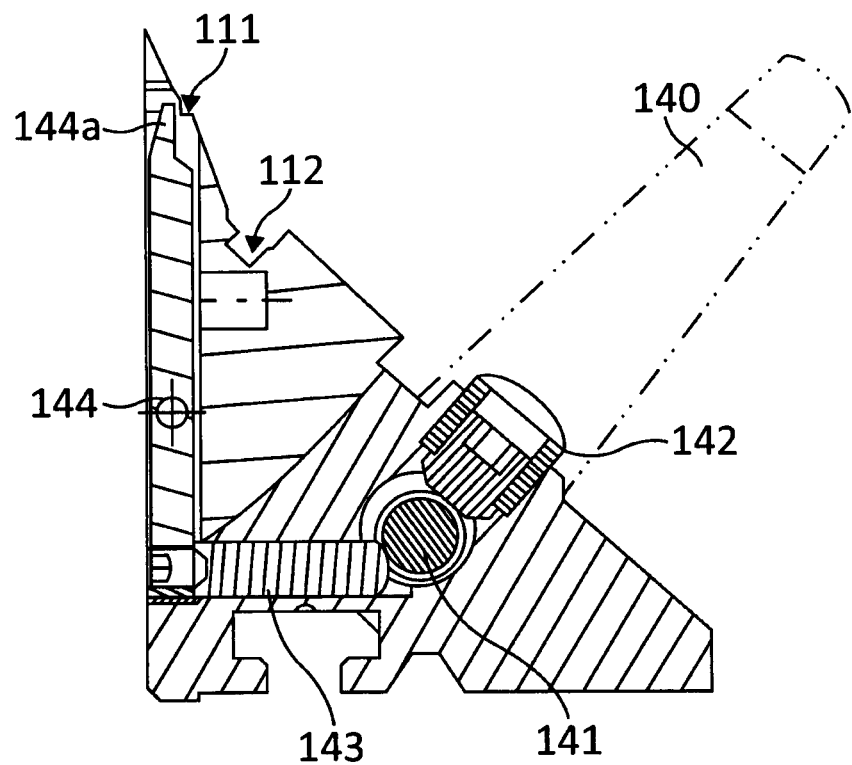

Located on knife block 110 is a clamping plate 130 that can be clamped against knife block 110 by way of a securing mechanism connected to an actuation element 140, so that a blade present in blade receptacle 111 can be secured. In the depiction, for example, the lever is in a zero position. An upward actuation of lever 140 results in a rotation of a cam 141 in such a way that a clamping bolt 142 pushes upward against clamping plate 130 located thereabove (not depicted in FIG. 5), so that a blade becomes clamped in place in first blade receptacle 111.

A downward actuation of lever 140 results in a rotation of cam 141 in such a way that a first ejector bolt 143 of an ejection means pushes outward against a second ejector bolt 144 of the ejection means, so that a tip 144a of second ejector bolt 144 pushes against a blade in first blade receptacle 111 and ejects it over the step. The blade can consequently fall into second blade receptacle 112 located therebelow.

The knife holder is embodied so that during introduction of a new blade 201 from the blade stack or blade supply container into first receptacle 111 via the first driver, a finger protector 150 that prevents injury from the moving blade is also slid out. Finger protector 150 can then be slid back again via a handle 151 in order to expose the blade in the blade position.

Figure 4:
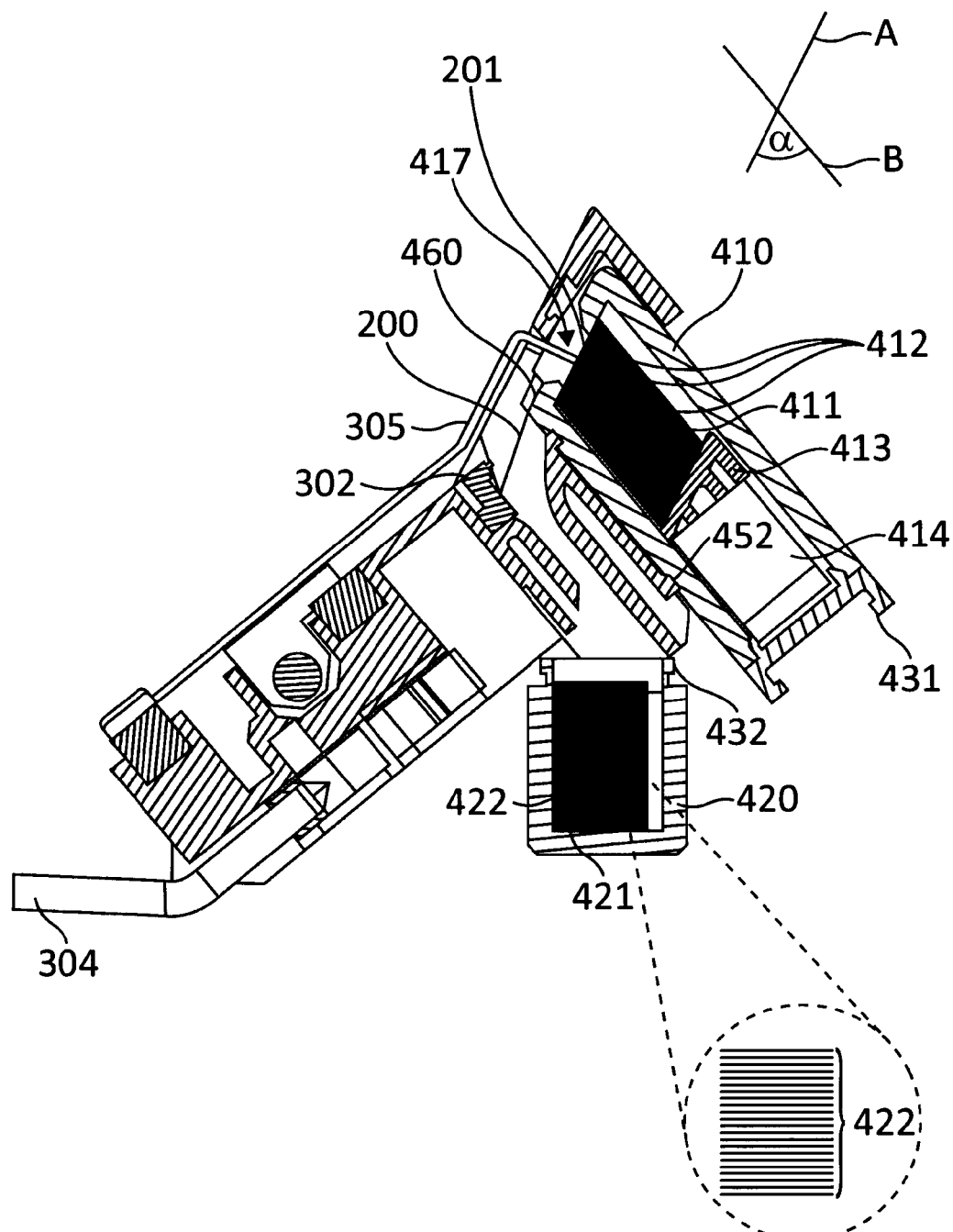
FIG. 4 is a cross-sectional view through the knife holder.

FIG. 4 furthermore depicts a blade supply container 410 externally mounted at a first external mounting location, as well as a blade disposal container 420 externally mounted at a second external mounting location, these together forming a blade dispenser. A blade stack 411 made up of a plurality of blades 412, 201 is received in blade supply container 410, the uppermost blade being labeled 201. Blade stack 411 is supported in a support block 413 that is impinged upon with spring force by a spring means embodied as leaf spring 414. The spring force presses the support block upward so that uppermost blade 201 of the blade stack comes to rest in a removal position next to a removal opening.

Figure 1A:
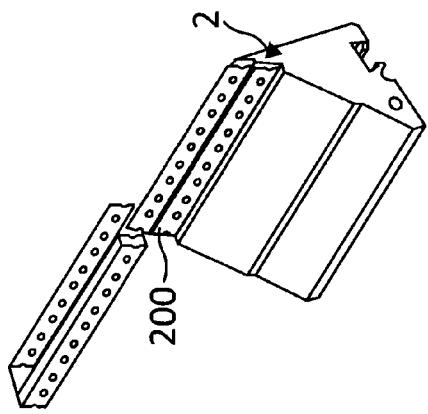
Figure 1B:
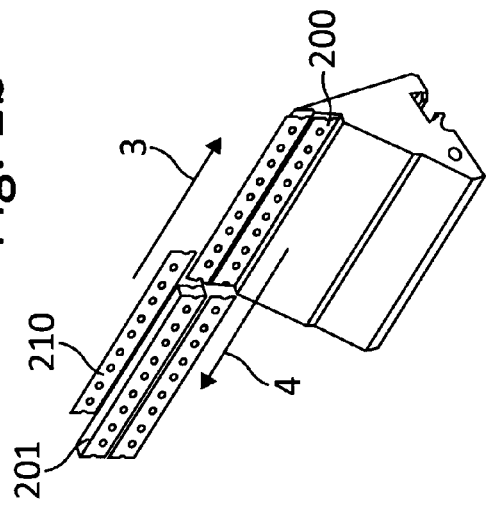
Figure 1C:
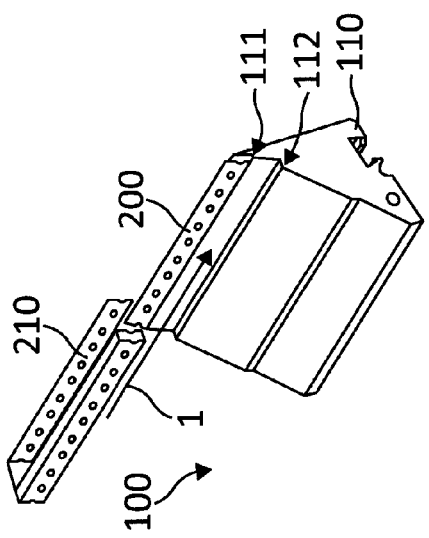
Figure 1D:
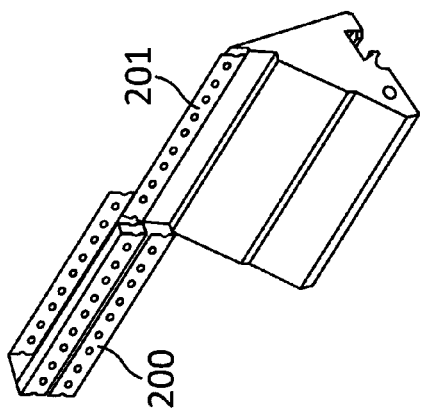
Figure 2:
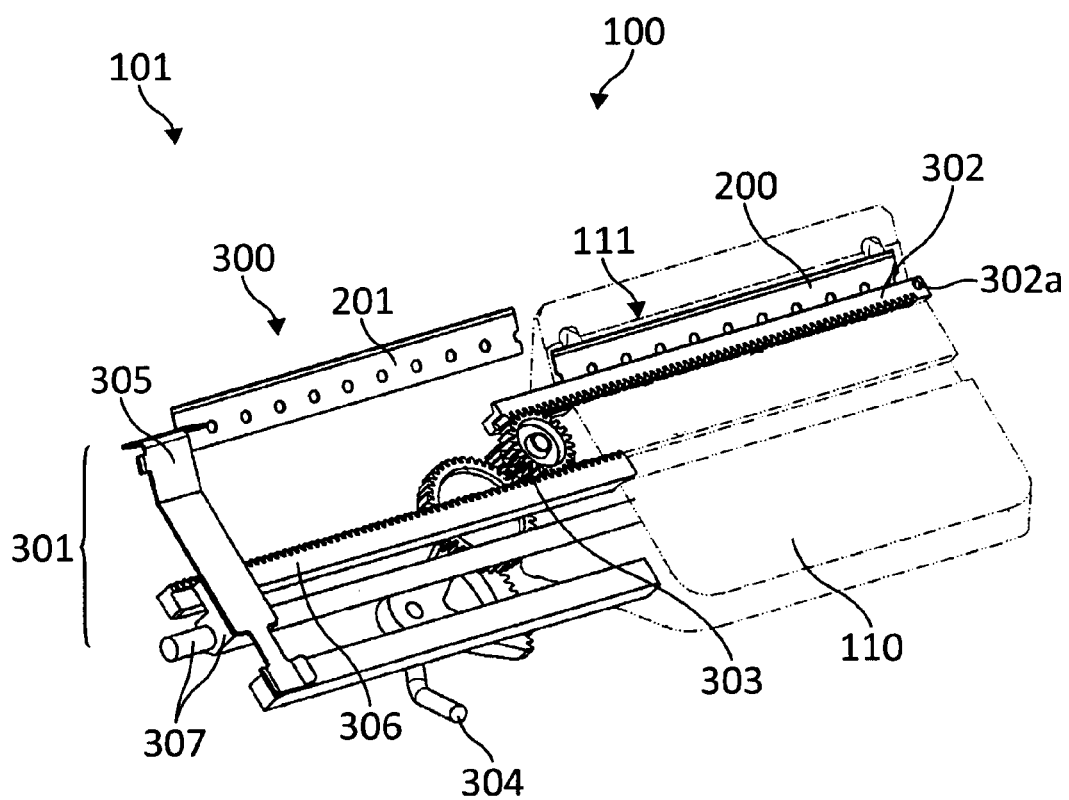
FIG. 2 depicts a solution in which first driver 301 and second driver 302 are actuated simultaneously via the driving mechanism. Be it noted, however, that actuation successively is also possible in the context of the invention.
Figure 3:
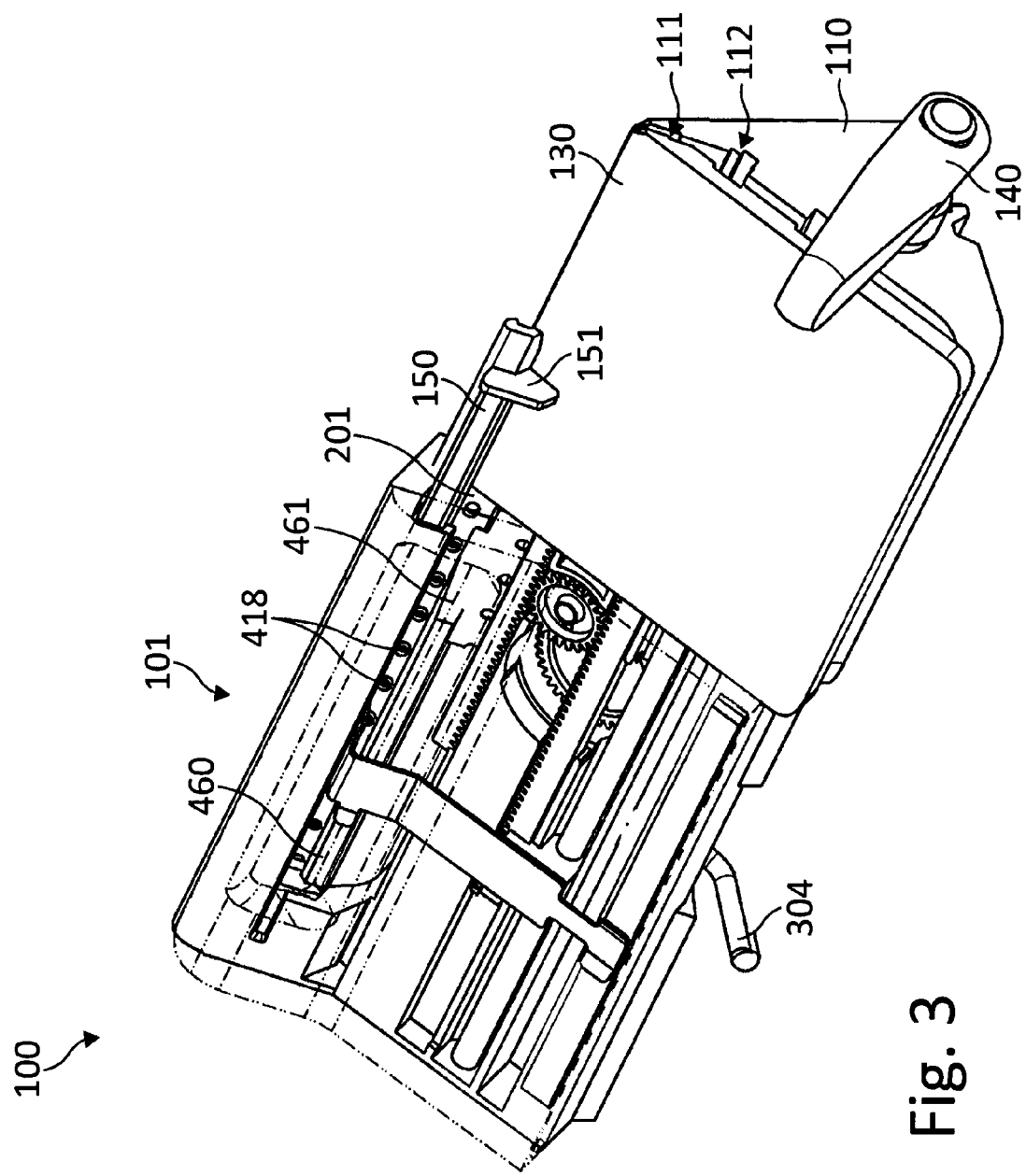
FIG. 3 is a schematic perspective depiction of knife holder 100.

The next blade to be removed is in this case always the uppermost one of blade stack 411. It can be slid out of the removal position and out of blade supply container 410 through the removal opening, to the side, i.e. to the right in FIG. 3, and removed. Each blade 412, 201 of blade stack 411 comprises one or more engagement openings 418 into which first driver 301 can engage in order to push the blade out of removal opening 416 of the blade supply container. In order to enable access to blade 201 in the removal position, an access opening embodied as a slot 417 is provided in the upper side of blade supply container 410.

Blade disposal container 420 is embodied here as a container open on its upper side. Blade disposal container 420 is embodied to receive used blades 422, which are likewise received as a stack 421 in blade disposal container 420. Blades to be disposed of fall from above into blade disposal container 420.

Blade dispenser 400 comprises a detachable and reconnectable connecting means that detachably connects blade supply container 410 and blade disposal container 420 to one another. The connecting means is embodied here as a slide closure in the manner of a dovetail guide, such that the connection can be released and created by sliding containers 410 and 420 with respect to one another. In the embodiment depicted, the dovetail guide comprises interengaging flanges 431 on the underside of the blade supply container and 432 on the upper side of the blade disposal container. As a consequence, the result of connecting the blade supply container and the blade disposal container is also that the upper side of blade disposal container 420 becomes closed off. One or both flanges 431 of the dovetail guide can preferably also be used to externally mount the respective container on the knife holder. In this case the knife holder comprises corresponding flanges of a dovetail guide.

Once blade disposal container 420 has been fastened on blade supply container 410 by means of the dovetail guide, the used blades are securely received and can easily be disposed of together with the empty blade supply container.

Blade supply container 410 comprises multiple alignment means that are embodied as grooves 452 and/or lugs and serve to enable exact orientation (and preferably secure fastening) of blade supply container 410 on knife holder 100. The knife holder preferably also comprises corresponding guides that interact with the alignment means of the containers, for example likewise lugs and/or grooves.

Blade supply container 410 furthermore comprises a bar 460 having a beveled end 461, which bar can serve as a guide for used blades. Beveled end 461 forms an inclined plane with respect to the blade supply container surface.

As is evident in the cross-sectional view in FIG. 4, the bodies or main extension planes A of blades 201, 412 of blade stack 411 are arranged with respect to stack direction B at an angle α not equal to 90°. The angle α between A and B is in this case approximately 70°. This enables a space-saving arrangement of blade supply container 410 on the knife holder. For this purpose, support block 413 is embodied in cross section with a corresponding angle α between its upper side, on which the blade stack is supported, and the vertical axis of the blade supply container. Support block 413 is impinged upon from below with spring force by leaf spring 414. The oblique placement of the blades in the blade supply container allows the horizontal installation space required for the blade supply container on the knife holder to be made smaller, since with a blade that extends approximately vertically, the blade supply container need not protrude horizontally but instead, as depicted, extends obliquely downward.

What is claimed is:

1. A knife holder (100) having a blade changing apparatus (101), the knife holder comprising:
   a first blade receptacle (111) defining a cutting position;
   a securing means (130, 141, 142) for securing a blade (201) received in the first blade receptacle (111),
   a second blade receptacle (112) defining an output position; and
   an ejection means (141, 143, 144a) for ejecting the blade (201) received in the first blade receptacle (111) out of the first blade receptacle (111);
   the first blade receptacle and the second blade receptacle being arranged in the knife holder in such a way that the blade ejected from the first blade receptacle (111) travels by gravity into the second blade receptacle (112).

2. The knife holder (100) according to claim 1, the first blade receptacle (111) and the second blade receptacle (112) being arranged vertically spaced apart in the knife holder (100).

3. The knife holder (100) according to claim 1, further comprising:
   a first mounting location for a blade supply container; and
   a first driver (301) for conveying a first blade (201) out of the blade supply container (410) into the first blade receptacle (111),
   wherein the blade supply container is mounted at the first mounting location.

4. The knife holder (100) according to claim 3, the first mounting location being arranged with a horizontal spacing from the first receptacle (111).

5. The knife holder (100) according to claim 3, further comprising:
   a second mounting location for a blade disposal container (420); and
   a second driver (302) for conveying a second blade (200) out of the second blade receptacle (112) into the blade disposal container (420);
   wherein the blade disposal container (420) is mounted at the second mounting location.

6. The knife holder (100) according to claim 5, the second mounting location being arranged with a horizontal spacing from the second receptacle (112).

7. The knife holder (100) according to claim 6, the first mounting location being arranged with a vertical spacing from the second mounting location.

8. The knife holder (100) according to claim 7, the first mounting location and the second mounting location being arranged on the same side of the first blade receptacle and next to the first blade receptacle (111).

9. The knife holder (100) according to claim 5, wherein the first driver (301) and the second driver (302) are coupled to a common driving mechanism (300), the common driving mechanism (300) being operable so that simultaneously the first blade (201) is conveyed out of the blade supply container (410) mounted at the first mounting location and conveyed into the first blade receptacle (111), and the second blade (200) is conveyed out of the second blade receptacle (112) into the blade disposal container (420) mounted at the second mounting location.

10. The knife holder (100) according to claim 1, further comprising an actuation means (140) coupled to the securing means and to the ejection means, wherein the actuation means is operable to actuate both the securing means and the ejection means.

11. The knife holder (100) according to claim 10, the actuation means (140) being a lever to be actuated manually.

* * * * *